(12) United States Patent
Toner et al.

(10) Patent No.: US 6,300,130 B1
(45) Date of Patent: *Oct. 9, 2001

(54) ULTRA RAPID FREEZING FOR CELL CRYOPRESERVATION

(75) Inventors: Mehmet Toner, Wellesley; Alex J. Fowler, South Dartmouth, both of MA (US)

(73) Assignee: The General Hospital Corporation and University of Massachusetts, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,915

(22) Filed: Nov. 16, 1998

(51) Int. Cl.[7] .................................. A01N 1/00; C12N 1/04; C12N 5/00; C12N 5/02
(52) U.S. Cl. ........................ 435/374; 435/1.3; 435/29; 435/325; 435/383; 435/243; 435/260
(58) Field of Search .................. 435/1.3, 29, 325, 435/383, 243, 374, 260, FOR 100, FOR 114, FOR 122

(56) References Cited

U.S. PATENT DOCUMENTS

| | | | |
|---|---|---|---|
| 4,676,070 | 6/1987 | Linner | 62/64 |
| 4,688,387 | 8/1987 | Conaway | 62/78 |
| 5,493,865 | 2/1996 | Wohlwend | 62/51.1 |
| 5,518,878 | * 5/1996 | Wilkins et al. | 435/1.3 |

OTHER PUBLICATIONS

G.M. Fahy et al., "Vitrification as an Approach to Cryopreservation," Cryobiology 21, 407–426 (1984).

Mehmet Toner et al., "Thermodynamics and kinetics of intracellular ice formation during freezing of biological cells," J. Appl. Phys. 67 (3) 1582–1593 (1990).

Peter Mazur, "Equilibrium, Quasi–Equilibrium, and Non–equilibrium Freezing of Mammalian Embryos," *Cell Biophysics* vol. 17, 53–92 (1990).

Peter Mazur et al., Contributions of Cooling and Warming Rate and Developmental Stage to the Survival of *Drosophila Embryos* Cooled to—205°C[1,2], Cryobiology 30, 45–73 (1993).

Jens O.M. Karlsson et al., "Fertilization and development of mouse oocytes cryopreserved using a theoretically optimized protocol," Human Reproduction vol. 11 No. 6, 1296–1305 (1996).

J.F. Peyridieu et al., "Critical Cooling and Warming Rates to Avoid Ice Crystallization in Small Pieces of Mammalian Organs permeated with Cryoprotective Agents," Cryobiology 33, 436–446 (1996).

* cited by examiner

*Primary Examiner*—David M. Naff
*Assistant Examiner*—Deborah K. Ware
(74) *Attorney, Agent, or Firm*—Nutter, McClennen & Fish

(57) ABSTRACT

A method for preserving biological material includes the steps of placing the biological material in thermal contact with a cryogenically coolable environment, applying radiant energy to the biological material to maintain the temperature of the biological material at physiological temperatures, cooling the surrounding environment to a temperature below the glass phase transition temperature of the biological material, and rapidly stopping the application of radiant energy to the biological material. The method produces cooling rates so rapid that the biological material is vitrified without an opportunity for ice crystals to form.

26 Claims, 8 Drawing Sheets

ULTRA RAPID FREEZING FOR CELL CRYOPRESERVATION

CROSS-REFERENCE TO RELATED APPLICATIONS

Not Applicable.

STATEMENT REGARDING FEDERALLY SPONSORED RESEARCH

Not Applicable.

FIELD OF THE INVENTION

The present invention relates to a method and apparatus for cryopreservation of biological material using ultra rapid freezing.

BACKGROUND OF THE INVENTION

With recent advances in cell transplantation, tissue engineering and genetic technologies, the living cell is becoming an important therapeutic tool in clinical medical care. From the use of living artificial skin and bone material to treat burn and trauma victims, to bioartificial devices and direct transplantation of cellular material to treat the increasingly long list of genetically-based diseases, living cells are increasingly incorporated into comprehensive treatment. In such a construct, the exogenous cells perform the multitude of complex tasks which the diseased tissue cannot. Successful long-term preservation and storage of mammalian cells is critical to the success of this type of medical care.

Conventional cryopreservation protocols rely on the addition of cryoprotectants to control the formation of damaging crystalline ice in the intracellular and extracellular liquid. The formation of ice in the extracellular liquid leads to dehydration of cells and has also been shown to catalyze the formation of intracellular ice [Toner et al., "Thermodynamics and kinetics of intracellular ice formation during freezing of biological cells," 67 *J.Applied Phys.* 1582–1593 (1990)]. The formation of intracellular ice directly damages the cell and usually leads to cell death.

Equilibrium and non-equilibrium cryopreservation protocols try to balance the deleterious effects of cell dehydration, exposure of the cells to toxic cryoprotectants and the lethal formation of intracellular ice so as to yield the highest possible percentage of viable cells [Mazur, "Equilibrium, Quasi-equilibrium, and non-equilibrium freezing of mammalian embryos," 17 *Cell Biophysics* 53–92 (1985)]. Protocols of this type have been very successful for certain cell types. For example, survival rates of greater than 90% have been reported for erythrocytes [Nei, "Freezing injury to erythrocytes I. Freezing patterns and post-thaw hemolysis," 13 *Cryobiology* 278–286 (1976)], pancreatic islets [Jutte et al., "Vitrification of Human Islets of Langerhans," 24 *Cryobiology* 403–411 (1987)] and mouse oocytes [Karlsson et al, "Fertilization and development of mouse oocytes cryopreserved using a theoretically optimized protocol," 11 *Human Reproduction* 1296–1305 (1996)].

There are many cell types, however, for which acceptable cryopreservation protocols have not been developed. This is largely due to the fact that the concentration of cryoprotectant required to avoid intracellular ice formation is too high for most cells to tolerate [Fahy et al, "Vitrification as an approach to cryopreservation," 21 *Cryobiology* 407–426 (1984)]. Among the important cell types for which successful and reliable freezing protocols have not been developed are hepatocytes, human oocytes, platelets and granulocytes.

The fact that human oocytes have not been preserved successfully in spite of the successful freezing of mouse oocytes illustrates another difficulty with the current methods of cryopreservation: they are extremely dependent on cell type. Even closely related cell types behave and survive differently when cryopreserved.

An alternative to conventional approaches to cryopreservation by freezing with high levels of cryoprotectant is vitrification, i.e., solidification of a liquid into an amorphous or glassy state as opposed to the crystalline state. Unlike the liquid-to-crystal transition, the liquid-to-glass transition is generally believed not to have any adverse biological effects. This is because there is no elevation in electrolyte concentration, no ice crystals to cause mechanical damage, and no potentially damaging osmotic shifts during the vitrification of cell suspensions.

It appears that nearly all liquids would undergo a transition to a glassy state if crystallization is bypassed on cooling. A necessary and sufficient condition for this transition is that the liquid solution should be rapidly cooled to the glass transition temperature so that nucleation and crystal growth cannot occur. Typically, the requisite cooling rates are very high for water (approximately $10^{7\circ}$ C./min), but they can be reduced to more workable levels (approximately $10^\circ$ C./min) by the addition of cryoprotectants (CPA, usually 50 to 60% w/w). However, CPA concentrations this high are typically lethal to biological cells. New methods of ultra-rapid cooling are needed to achieve glassy state during cooling of biological cell suspensions.

The formation of intracellular ice during freezing may be avoided by hyperquenching the cells. In hyperquenching the water is cooled so quickly that nucleation events do not occur and the liquid undergoes a glass phase transition. As liquid water is cooled below its freezing point, it becomes energetically favorable for nucleation to occur. At 130K, however, liquid water goes through a glass phase transition, which is a second order thermodynamic phase transition, and the relaxation time for the molecules becomes greater than laboratory time scales—i.e., the viscosity of the fluid increases so that molecular rearrangement into crystals becomes impossible. If one can get water to the glass phase before ice crystals nucleate, then one creates an amorphous solid referred to as either amorphous solid water or amorphous ice.

There are a number of ways to form glass phase solid water; water vapor deposition on to cryo-cooled plates at very low pressures, exposing crystalline ice to very high pressures at temperatures below 130K and thereby crushing it to the glass phase, and spraying water micro-droplets at supersonic velocities onto cryoplates. None of these techniques, however, is suitable for use in freezing cells. Water vapor deposition simply cannot be done with a cell, and the other two methods expose the cell to lethal stress.

In order to preserve the wide variety of cellular material needed in current medical procedures, a new method of ultra rapid cooling that can successfully cryopreserve biological material without the formation of intracellular ice is needed. Such a method must avoid the use of high concentrations of CPAs which are toxic to many cell types and not expose the biological material to damaging physical stresses.

SUMMARY OF THE INVENTION

The technique of ultra-rapid freezing uses spatially confined heating to hold tissue samples warm while freezing the surroundings to cryogenic temperatures. Upon removal of the heating the sample freezes very rapidly due to direct thermal contact with the surrounding material. Numerical calculations indicate that freezing rates of up to 1 million degrees per second can be achieved with this technique. This freezing rate is so fast that the sample will not freeze into a crystalline solid such as ordinary ice, but into a glass phase solid that has no crystals, i.e., the sample is vitrified.

The method includes placing a cellular material sample in thermal contact with a cryogenically coolable environment. The cryogenically coolable environment is maintained at a temperature below the glass phase transition temperature of the cellular material while at least a portion of the cellular material is maintained at physiological temperatures by spatially confined heating. The spatially confined heating is then stopped resulting in the cooling of the cellular material. This method results in cooling rates greater than $10^{5°}$ C. per second, and even cooling rates greater than $10^{6°}$ C. per second, resulting in the vitrification of the cellular material.

In specific embodiments, the spatially confined heating may be provided using a radiant energy source that is at least partially absorbed by the cellular material or by the water found within the cellular material. The cryogenically coolable environment may be provided by a cryostage or, in one embodiment, by suspending the cellular material within a hole formed in a high thermal conductivity material.

Material cryopreserved using the method of the invention may be recovered by warming the material at a warming rate sufficiently high so as to prevent devitrification, i.e. the nucleation of ice crystals from the glass phase during thawing.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

A cryopreservation method of the invention includes using radiant energy to provide spatially confined heating to a region of biological material while cooling the surrounding environment to temperatures below the glass phase transition temperature of the biological material. The glass phase transition temperature is about 130K for pure water, higher for aqueous solutions. Accordingly, the glass phase transition temperature for the biological material will be about 130K, but may be higher if intracellular cryoprotective agents (CPAs) are added. Sudden removal of the heat source results in cooling rates so fast that the intracellular solution forms a non-crystalline glass phase without forming damaging ice crystals. The cryogenically frozen biological material sample can then be warmed at moderate to fast warming rates so that devitrification (the nucleation of crystals from the glass phase) does not occur during thawing, and the entire cryopreservation process can be completed without forming ice crystals inside the cell.

Figure 1:
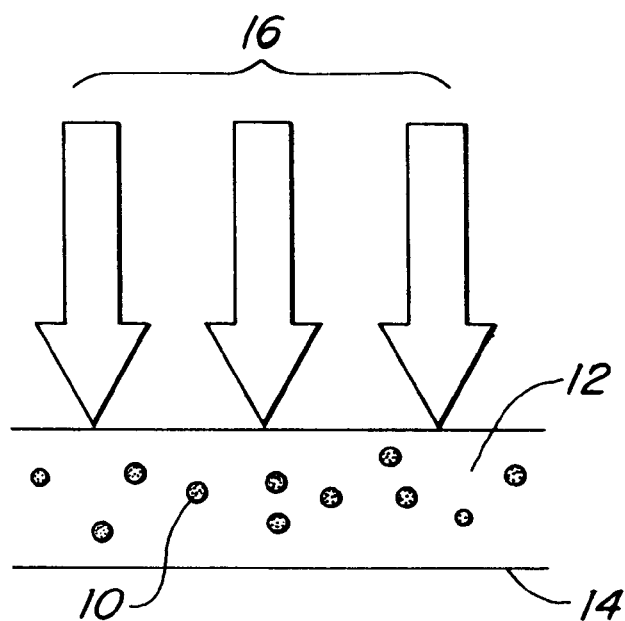
FIG. 1 illustrates a step in the method of the invention wherein spatially confined heating is provided by radiant energy supplied to suspended biological tissue.

Spatially confined warming of a biological tissue sample can be achieved in a number of ways. As illustrated in FIG. 1, the biological tissue 10 can be suspended in a solution 12 that is placed into contact with a cryogenic cooling plate 14. The spatially confined warming can be provided by applying radiant energy 16 that is selectively absorbed by the tissue 10 and not by the surroundings. For example, the radiant energy 16 may include the use of laser energy having a wavelength of 577 nm to target erythrocytes as a suspended biological tissue sample 10 for warming in a saline solution 12—the erythrocytes absorbing energy having that wavelength while the surroundings do not. Alternatively, 2 micron radiation can be used to target the water in biological tissue 10 surrounded by a non-absorptive material such as silicon oil 12.

In the described spatial heating configuration, the heating only occurs in the biological tissue 10 and the tissue 10 can be held at physiological temperatures (between approximately 0 to 40° C.) while the surroundings are cooled by cryoplate 14. When the spatially confined heating is removed, by stopping the application of the radiant energy 16 to the biological tissue, the biological tissue 10 cools rapidly. Using the cryopreservation method of the invention, resulting cooling rates can be as high as 1 million degrees per second for a 10 micron diameter biological tissue sample. The cooling rate will decrease as the diameter of the sample squared increases.

Figure 2:
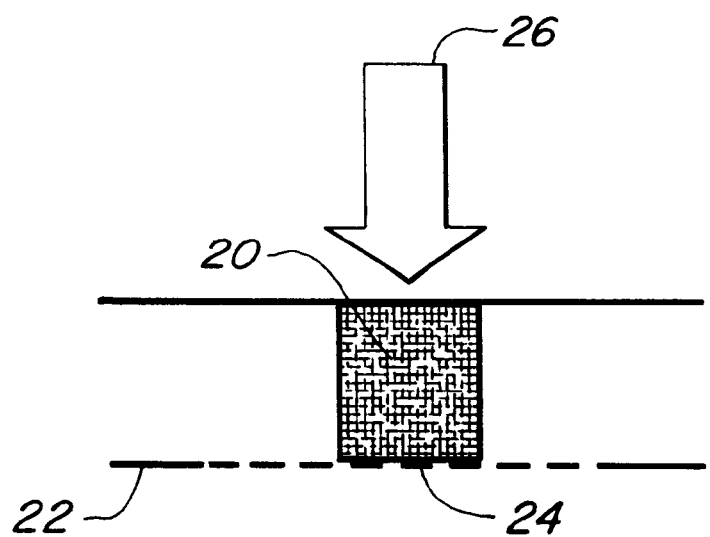
FIG. 2 illustrates a step in the method of the invention wherein spatially confined heating is provided by a focused beam of radiant energy to a biological tissue sample located on a cryostage over an adiabatic region.

Another way in which spatially confined heating can be achieved is to use a strongly focused beam of energy that is absorbed by both the biological tissue and surrounding medium. One method for cryopreserving biological material of the invention using this approach is illustrated in FIG. 2. Biological tissue sample 20 can be cooled from below by a surface 22 that has an adiabatic center region 24 while a focused beam of laser or microwave energy 26 maintains at least a portion of the sample at physiological temperatures.

Figure 3:
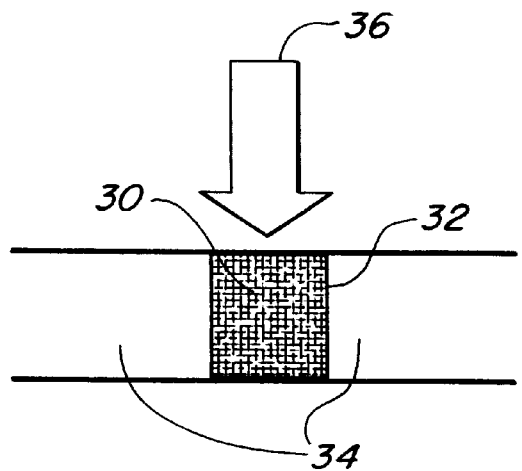
FIG. 3 illustrates a step in the method of the invention wherein spatially confined heating is provided by a focused beam of radiant energy to a biological tissue sample located in a well formed in a high thermal conductivity material that has been cooled.

In an additional method of the invention illustrated in FIG. 3, biological tissue sample 30 is cooled peripherally by being injected into a hole 32 that has been drilled into a material having a high thermal conductivity 34 that is cooled to cryogenic temperatures. Biological tissue sample 30 can also be maintained at physiologic temperatures by applying a focused beam of laser or microwave energy 36 to the sample 30. Numerical experiments indicate that a cylindrical region of the sample can be held between 0 and 37° C. if the sample is either cooled from below by a surface that has an adiabatic center region, or if the sample is cooled peripherally by being injected into a hole that has been drilled in a high conductivity material. Once again cooling rates of up to 1 million degrees per second can be achieved for regions 10 microns in diameter when the radiant energy is suddenly removed.

By using planar heat sources and computer controlled stages, this technique could be used to freeze large numbers of cells or tissue samples.

Once vitrified, samples may be stored at cryogenic temperatures. A sample may be recovered by warming at moderate to fast warming rates so that devitrification (the nucleation of crystals from the glass phase) will not occur. Thus, the entire cryopreservation process can be completed without any crystals forming inside the cell.

EXAMPLE 1

Numerical Model

Construction of a numerical model answers two fundamental questions about the cryopreservation method of the invention. The first is how large a sample region can be held between 0 and 40° C. by laser warming while the surroundings are cooled to $T_c$. The second is how fast the cooling rate will be once the laser heating is removed.

Figure 4:
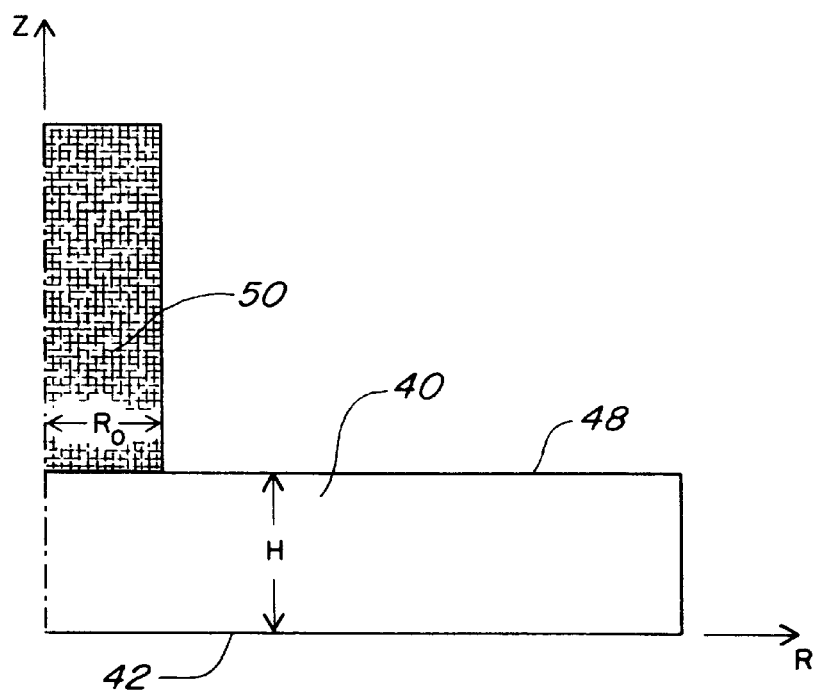
FIG. 4 illustrates diagrammatically the step shown in FIG. 2.
Figure 5A:
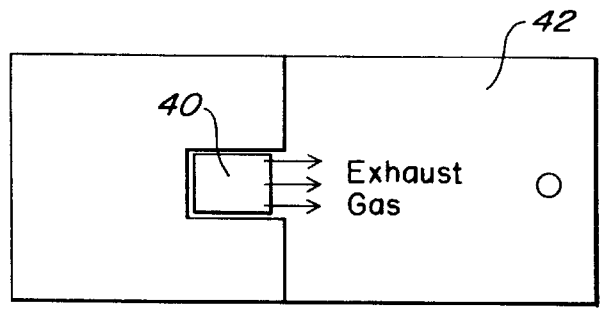
FIGS. 5A and B illustrate top and side views, respectively, of a cryostage useful with the method of the invention.
Figure 5B:
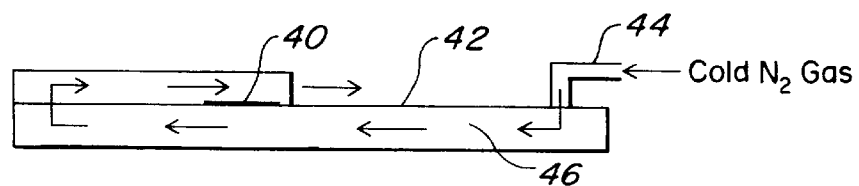

The basic geometry of the computational system is illustrated diagrammatically in FIG. 4. Cells which are either in suspension or attached to a glass surface as a sample 40 are cooled from below on a cryostage 42 at a temperature $T_c$. An example of such a sample 40 and cryostage 42 is shown in FIGS. 5A and 5B. Cryostage 42 may suitably be constructed of Lexan and is designed specifically to prevent condensation on the sample surface so that laser energy is not diverted from the sample 40. Nitrogen ($N_2$) gas is forced through a copper coil immersed in liquid nitrogen (not shown). The cold $N_2$ gas then flows through an insulated tube 44 to the cryostage 42 where it enters an internal channel 46 and passes under the sample. The cold $N_2$ gas is then redirected back to exhaust over the top of the sample 40 where it creates a moisture free layer. In this way, sample 40 can be cooled to −196° C. without condensation forming on the sample surface.

Returning to the numerical model, the top 48 of sample 40 is exposed to gas and thus will have negligible heat transfer compared to that through the conducting bottom surface. As sample 40 is cooled, a laser 50 holds a small region of the sample at a temperature between 0 and 40° C. so that the cells are neither damaged by excessive heat nor frozen.

The system is modeled as an axi-symmetric two-dimensional system in cylindrical coordinates. The conservation of energy equation can be nondimensionalized to the form:

$$\tilde{c}\frac{\partial\theta}{\partial\tau} = A^2 \frac{\partial}{\partial Z}\left(\tilde{k}\frac{\partial\theta}{\partial Z}\right) + \frac{\partial}{\partial R}\left(\tilde{k}R\frac{\partial\theta}{\partial R}\right) + \tilde{Q} \quad (1)$$

where the dimensionless variables are:

$$R = \frac{r}{R_0} \quad Z = \frac{z}{H} \quad \tau = \frac{\alpha\tau}{R_0^2} \quad A = \frac{R_0}{H} \quad (2)$$

$$\theta = \frac{(T - T_c)}{(T_0 - T_c)} \quad \tilde{k} = \frac{k}{k_f} \quad \tilde{Q} = \frac{q \& R_0^2}{k_f(T_0 - T_c)} \quad (3)$$

$$\tilde{c} = \frac{\rho c}{\rho f_f} \quad (4)$$

In these equations $R_0$ is the radius of the laser heating, $k_f$, $c_f$ and $\rho_f$ are the thermal conductivity, specific heat and density of the fluid phase. $T_c$ is the temperature of the cold boundary. $T_0$ is the equilibrium melting temperature of the ice. H is the height of the liquid/ice layer (the thickness of the layer) and q is the rate of volumetric heating due to the laser. The material properties are modeled as phase dependent, but not temperature dependent within a single phase. The thermal conductivity of crystalline ice is modeled as 4 $k_f$ and the product $\rho_c$ of the crystalline ice was modeled as $\rho_c c_f/2$ [White, F. M., *Heat and Mass Transfer*, Addison-Wesley, Reading, Mass. (1998)]. It is not clear whether the effect of modeling the thermal properties as temperature dependent in addition to phase dependent would increase or decrease the calculated freezing rate since both k and c tend to decrease with temperature. The thermal conductivity of liquid water, moreover, changes by less than a factor of two over the 400 Kelvin degrees for which data is available [Bejan, A., *Heat Transfer*, Wiley and Sons, New York, N.Y. (1993)]. Neglecting the temperature dependence, therefore, will have only a small effect on the calculated cooling rates.

The system is heated volumetrically by the laser in the region R<1. Uniform heating is assumed within the irradiated region. In the actual system, the heating would decrease with depth as the laser energy is absorbed; but approximately uniform heating can be achieved by selecting a laser wavelength with a small coefficient of absorption. The disadvantage of this technique is that it requires increased laser power. In the region R>1, there is no volumetric heating. The first boundary conditions studied were negligible heat transfer at the top surface (Z=1) and an isothermal bottom surface (Z=0) at temperature $T_c$ ($\theta$=0). A symmetry condition is imposed at R=0 and T=$T_c$ at the edge of the computational domain R=$R_{edge}$.

In order to solve for the cooling rate once the laser has been turned off (Q=0), an initial condition must be available that is the steady state solution with the laser turned on. This steady solution must be such that there is a fluid region in which cells would not become crystallized (T>0° C.), but the maximum temperature must not be so hot that the cells are damaged (less than 40° C.). Q must be adjusted until the maximum temperature in the system is approximately 40° C.

Figure 6:
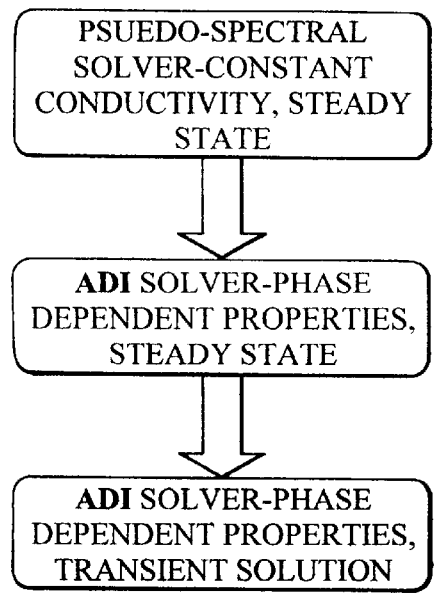
FIG. 6 illustrates a sequence of steps for computing a solution for a numerical model of the method of the invention.

The sequence of techniques used in computation of the solution is illustrated in FIG. 6. The steady state solution is developed in two steps. In the first step, a combined spectral and finite difference method is used to obtain a rough solution. If the thermal conductivity is assumed to be constant throughout the computational domain, the dimensionless temperature can be represented by a Fourier series of the form:

$$\theta = \sum_{n=1,3,5} a_n(r) \sin\left(\frac{n\pi}{2}Z\right) \tag{5}$$

Plugging this into the steady state energy conservation equation and making use of the orthogonality of sines results in a second order ordinary differential equation (ODE):

$$A^2 \frac{a_n(n\pi)^2}{4} - \frac{d^2 a_n}{dR^2} - \frac{1}{R}\frac{da_n}{dr} = \frac{4}{n\pi}\overline{Q} \tag{6}$$

The boundary conditions in R become:

$$\frac{da_n}{dr} = 0 \text{ at } R = 0 \tag{7}$$

and $$a_n = 0 \text{ at } R = R_{edge} \tag{8}$$

The ODE is solved by using finite difference discretization and taking 15 modes in the series. The resulting linear system of equations is solved using a successive over-relaxation (SOR) iterative scheme.

This solution and the Q value found are then used as an initial condition for a two dimensional finite-difference scheme in which the thermal conductivity is modeled as phase dependent. The two-dimensional finite-difference system with variable conductivity is solved using an alternating direction implicit (ADI) method, a second order accurate time-stepping scheme that can be used for both steady state and transient analysis. The convergence criteria for the steady state solution is that the maximum relative error be less than 0.001.

The cooling rate when the laser is turned off is calculated using the same ADI finite difference scheme. The cooling rate is defined as the instantaneous rate of cooling when the temperature of a liquid region dropped below $\theta=0.27$ (T=130K).

The reported solutions are generated using $\Delta R=0.2$ and $\Delta Z=0.2$, $\Delta\tau=0.001$ and $R_{edge}=4+R_{adiabatic}$ ($R_{adiabatic}$ is an adiabatic center region that is necessary for the computation and is described below). Convergence tests indicate that the calculated cooling rates change by less than 0.5% when $\Delta R$ and $\Delta Z$ are halved, and by less than 2% when $\Delta\tau$ is reduced by a factor of 10. $R_{edge}$ is chosen so that less than 2% of the total heat transfer occurred through the $R=R_{edge}$ surface.

The combined finite difference and spectral method converges very quickly. The convergence criteria is set as the maximum error being smaller than 1e-4. Different Q values are tried until a value of Q is found that gives a maximum temperature of about $\theta=1.2$, which corresponds to 39.2° C. if $T_c=77K$ and $T_0=273K$. The Q value and steady state solution are then refined using the ADI solver with phase dependent conductivity. Q is adjusted until $\theta_{max}$ was within 3% of 1.2.

Figure 7:
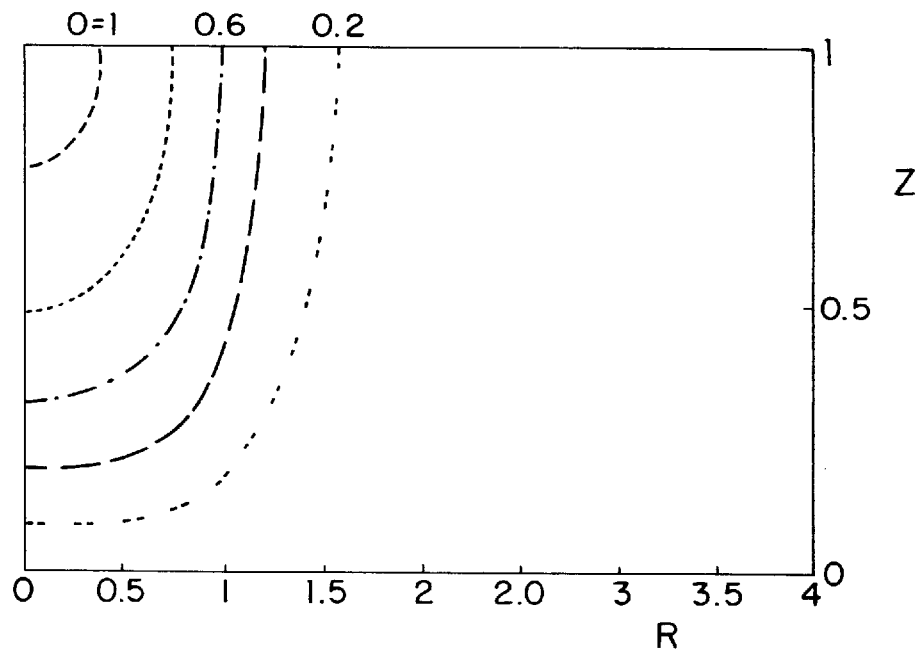
FIG. 7 graphs isotherms for a radiant energy warmed biological tissue sample on a cryostage against the radius (R) and height (Z) of the sample.

Isotherms of the steady state solution found using this technique for aspect ratio A=1 are shown in FIG. 7. The region inside the first isotherm ($\theta>1$) is liquid water. It can be seen from FIG. 7 that having a bottom boundary held at 77K results in a region of liquid water that is too small in which to reliably place a cell. Changing the aspect ratio does not result in a more suitable liquid region.

Figure 8:
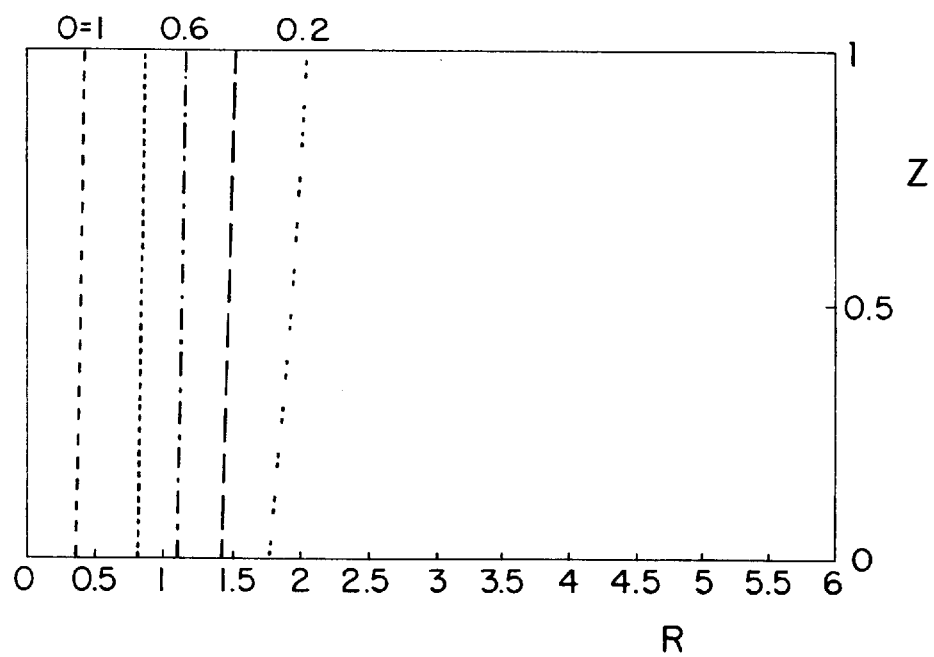
FIG. 8 graphs isotherms for a radiant energy warmed biological tissue sample on an adiabatic region on a cryostage against the radius (R) and height (Z) of the sample.

In order to increase the size of the liquid region, the bottom boundary condition is changed so that an adiabatic region of radius $R_{adiabatic}$ extends out from the center of the sample. FIG. 8 illustrates the isotherms when the aspect ratio A=1 and the adiabatic region radius is twice that of the laser beam, i.e., $R_{adiabatic}=2$. One can see that the liquid region extends all the way to the bottom of the sample. This is a suitable liquid region in which to place cells reliably.

This steady state solution is used as the initial condition for the ADI time-stepping scheme used to calculate cooling rates. The instantaneous cooling rates are calculated for points originally in the liquid region as they pass through the glass phase transition temperature $\theta_g=0.27$. The dimensionless cooling rates are fairly uniform throughout the liquid domain at 1.68. If the laser beam diameter is taken to be 10 microns, this indicates a cooling rate of greater than $10^6$K per second.

One method for creating a sample with an adiabatic center region is to drill a hole in the sample slide with hydrophobic walls so the sample liquid would not creep down into the hole. Alternatively, a hole could be drilled into a high conductivity material such as platinum of sapphire (which are both non-toxic to the cells) and the sample could be injected into the hole. Numerical simulation of this configuration was performed as well and it was found that these two techniques result in almost identical cooling rates.

The numerical models indicate, therefore, that by careful choice of geometry a cell can be held warm by a laser while the surroundings are cooled to 77K.

EXAMPLE 2

Freezing of Dilute Aqueous Solutions

Experiments show that cooling rates similar to those predicted with the numerical model can be achieved during the freezing of dilute aqueous solutions. These experiments demonstrate that one can achieve an amorphous solid ice using laser warming with solutions that are much more dilute than those currently required to achieve vitrification with conventional freezing techniques.

The samples consist of a layer of aqueous solution sandwiched between two parallel glass plates separated by distances from 10 to 100 microns. The solutions used in these experiments are sucrose solutions ranging from 0 to 2 molar. In addition to the sucrose, 0.015 M of Amaranth (FD&C Red Dye #2) are added. The dye is necessary because the laser used produces a beam at 532 nm which is not absorbed by water. Spectrophotometric analysis indicates that 0.015 M Amaranth would cause 10% to 50% of the beam energy to be absorbed in passing through the liquid layer, depending on the layer thickness.

The sample was placed on cryostage 42 (FIGS. 5A and 5B) constructed of Lexan. Temperature of the sample can be monitored by a type T thermocouple imbedded in the ice. When the temperature reaches the desired level, the laser is fired. The laser is capable of delivering a 400 mJ pulse in 7 ns. The energy delivered per pulse is adjusted until the firing of the laser results in a clear region without gas bubbles. The sample is then warmed by reducing the gas flow rate, or by reducing the contact area between the copper coil and the liquid nitrogen.

Figure 9:
FIG. 9 shows photographs of a 0.5 Molar sucrose solution after laser melting and rapid solidification, the sample on the left has been frozen to −150° C., the same sample is shown on the right having "recrystallized" at −30° C.

Initial experiments demonstrated that a clear region could be created for solutions of 2M, 1M and 0.5M sucrose. FIG. 9 provides pictures taken of clear regions produced by laser warming and rapid pictures taken of clear regions produced by laser warming and rapid refreezing of 0.5M sucrose solution. The clear regions are completely transparent, as is liquid water, but at −30° C. the ice becomes opaque once again. The return to opacity at temperatures well below the melting point indicates that the clear regions are not a result of photo-bleaching or some laser induced chemical reaction. The ice appears to return to its original state.

EXAMPLE 3

Rapid Freezing of Dilute Aqueous Solutions with X-ray Diffraction Analysis

A testing method and apparatus have been devised to provide x-ray diffraction analysis of solutions cooled by the method of the invention. In the test procedure, the sample is cooled to below the glass phase transition temperature of the solution (130K for pure water, higher for aqueous solutions) by submerging it in liquid nitrogen and maintained at that temperature. A portion of the sample is laser warmed. The laser is then turned off, and the warmed portion of the sample is rapidly cooled as described above. The sample must then be transferred into the x-ray diffractometer without raising the temperature above 150K. Often, transfer of the samples to the diffractometer results in exposure of the sample to room air which causes crystalline ice to immediately form on the sample. To avoid this a sample holder is used that can be placed directly into the diffractometer without exposing the sample to room air. X-ray diffraction results may then confirm the presence of amorphous ice produced by the method.

Figure 10:
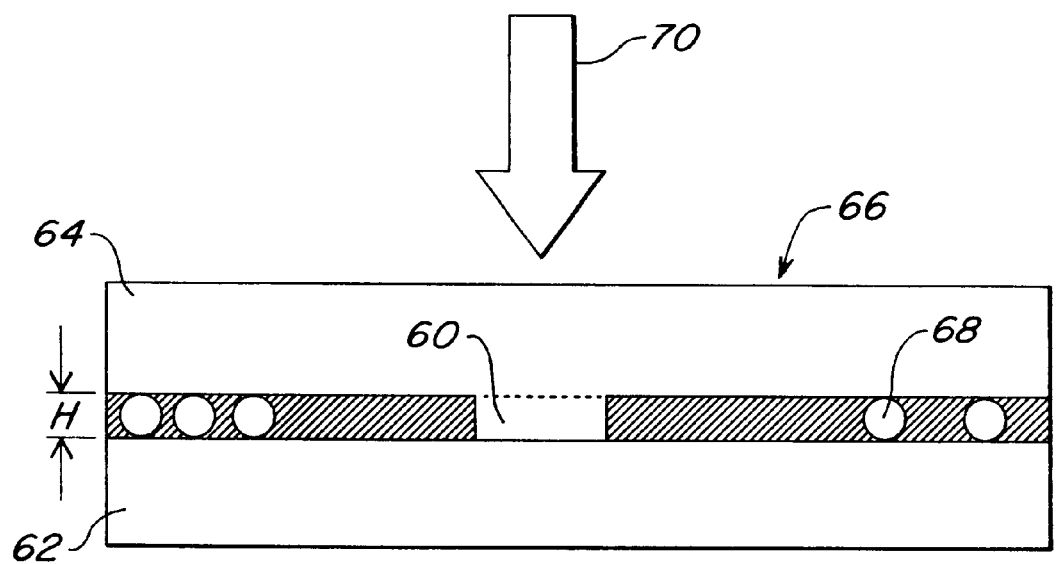
FIG. 10 shows a sample slide constructed for use in holding a dilute aqueous solution for rapid freezing.

Rapid solidification of the dilute aqueous solutions is accomplished by first injecting solution into a channel 60 of known height H between two glass coverslips 62, 64 to create a sample slide 66 as shown in FIG. 10. The height of channel 60 is controlled by mixing cross-linked polystyrene microbeads 68 of known diameter into a UV curing glue. The glue is spread along the edges of one coverslip 62 and the second coverslip 64 is pressed onto the first. The glue is then cured by exposure to a UV lamp. The height of the channel 60 can be measured by using a micrometer to measure the total height of the resulting slide and subtracting the thickness of the individual coverslips 62, 64.

The aqueous solutions are mixtures of distilled water and sucrose. In order to selectively heat the aqueous solution, a laser pulse 70 at 532 nm is used. The aqueous solutions also contained 0.005 M ameranth (FD&C Red Dye #2) which absorbs strongly at 532 nm. By testing varying dye concentrations over a large range it was determined that the absorbance of 532 nm radiation was linearly related to dye concentration. Based on this relationship, a 0.005 M dye solution absorbs less than 5 % of the energy incident on a 10 micron layer. This low absorbance was selected so that roughly uniform heating could be achieved throughout the layer of solution in the sample slide 66. The laser used to deliver the pulse is a Q-switched YAG capable of delivering 400 mJ of energy in a 7 nanosecond pulse.

Figure 11A:
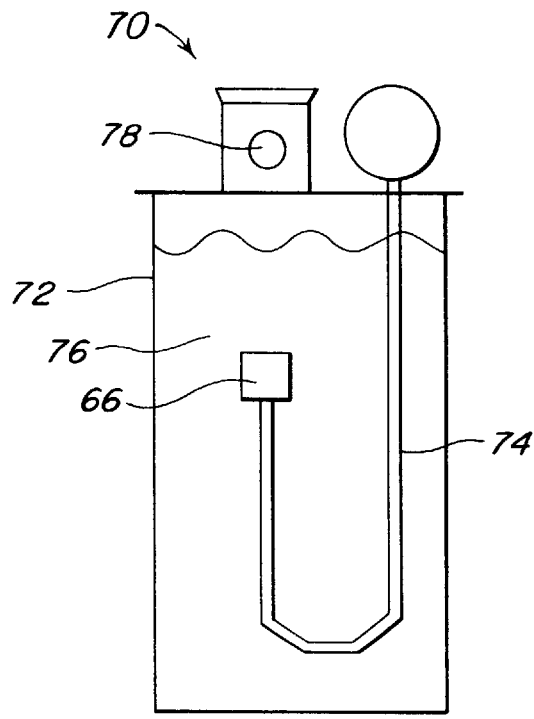
FIGS. 11A and B illustrate a sample holding apparatus for use in preparing and testing rapidly frozen samples.
Figure 11B:
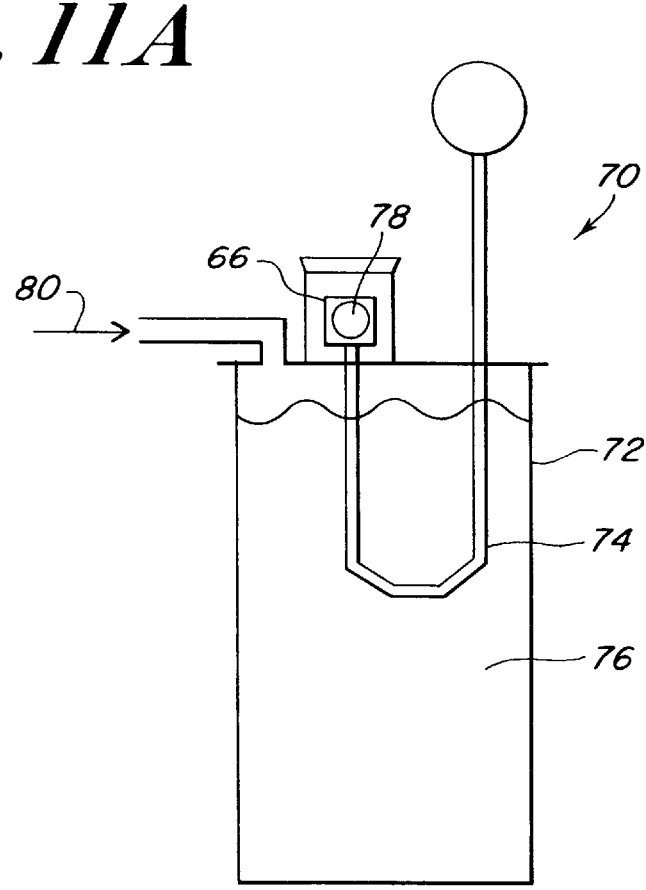

The sample holding apparatus 70 used consists of a Dewar flask 72 with a copper J-bar 74 that could be lowered (FIG. 11A) and raised (FIG. 11B) in and out of a liquid nitrogen bath 76. A copper clamp machined into the end of the J-bar 74 holds the sample 66. The apparatus 70 includes a hole 78 through which the laser and the x-ray beam can be aimed. When the sample 66 is in a raised position, a supplementary flow of cold nitrogen gas 80, provided by either the x-ray diffractometer or by an auxiliary tank, creates a strong outward flow of nitrogen gas through hole 78 that prevents condensation from accumulating on the sample 66. Experiments performed with thermocouples imbedded in glass slides show that the sample temperature remains within 5° C. of the gas temperature for temperatures cooler than –100° C.

Sample 66 is held in the raised position to deliver the laser energy through hole 78. Nitrogen gas 80 is forced through a copper coil immersed in liquid nitrogen and injected into the apparatus. The gas temperature near the sample was measured via thermocouple and the gas flow rate adjusted until the gas temperature was –165° C. The laser supplied a beam of energy focused to a diameter of 2.8 mm and Q-switched pulses were delivered at different power settings until a region of clear ice formed in the sample 66 that did not contain bubbles. A laser fluence of about 1.1 J/cm$^2$ was optimal. After a clear region is created in the sample 66, the sample is lowered into the liquid nitrogen bath 76 and the sample holding apparatus 70 is transported to the x-ray diffractometer.

A Seimens SMART System CCD diffractometer was used for the x-ray analysis. The built-in nitrogen gas supply temperature was adjusted to –165° C. and the sample holding apparatus 70 was inserted into the diffractometer. The built in nitrogen gas supply was connected to the top of the apparatus 70 and the sample 66 was raised into position and adjusted so that the x-ray beam struck the sample in a control region of crystalline ice so that a baseline crystal pattern could be recorded. The sample 66 was then repositioned so the beam passed through the rapidly solidified ice. X-ray diffraction patterns were recorded on a 6.18 cm CCD using a 60 second exposure. The x-ray beam was a 0.5 mm collimated beam from a Molybdenum source.

Figure 12A:
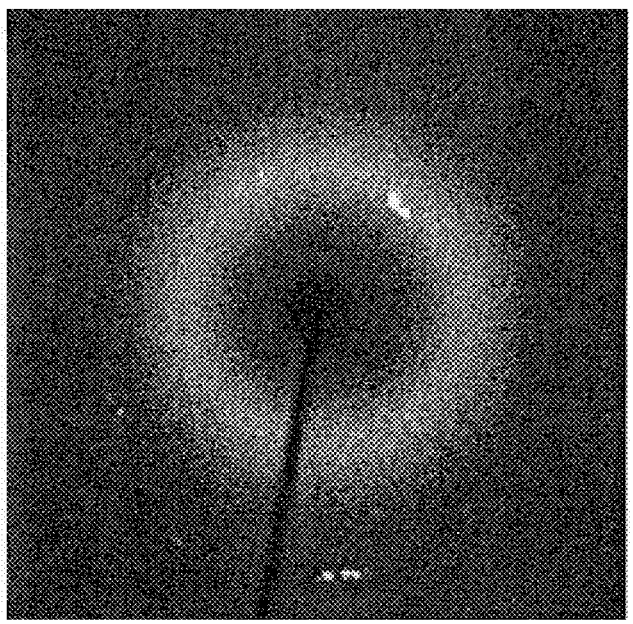
FIGS. 12A and B illustrate x-ray diffraction results for a crystalline ice sample (A) and a rapidly frozen amorphous ice sample (B)
Figure 12B:
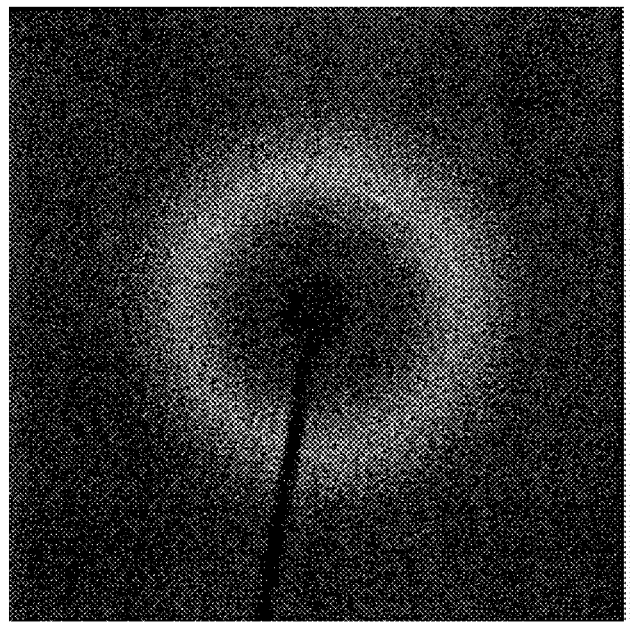
Figure 13A:
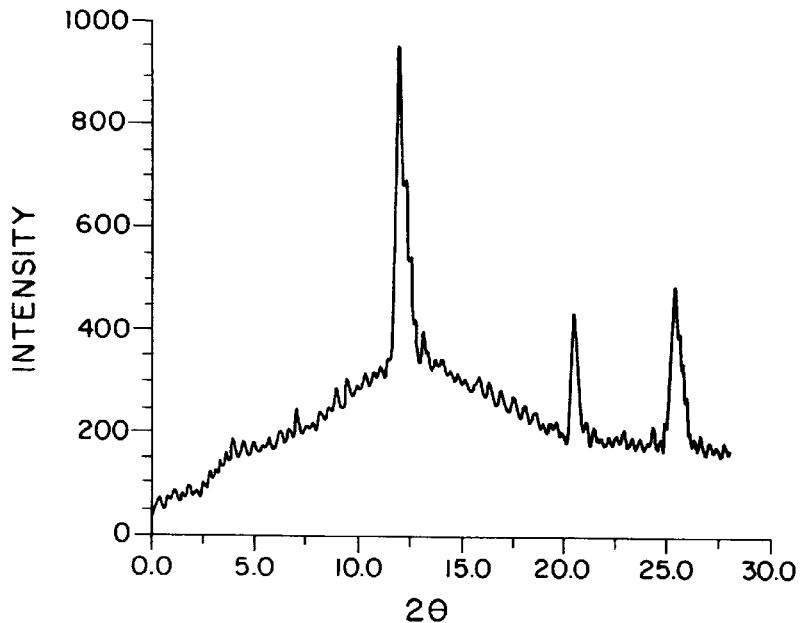
FIGS. 13A and B plot maximum intensity of x-ray diffraction images as a function of diffraction angle for a crystalline ice sample (A) and a rapidly frozen amorphous ice sample (B).

FIGS. 12A and 12B show the x-ray diffraction images obtained from a region of pure crystalline ice (12A) and laser created amorphous ice (12B) at different positions of the same slide having a sample of 1 M sucrose solution and a channel height H (FIG. 10) of 21 microns. The broad amorphous scattering in both images is a result of the glass slides surrounding the ice, but bright spots appearing in FIG. 12A both within the ring of diffuse scattering and beyond it indicate the presence of crystals. The lack of apparent bright spots in FIG. 12B suggests that the sample is amorphous. In order to determine whether any crystalline peaks were present in the laser treated region, the x-ray image was analyzed by a computer code that searched for the maximum intensity within the sample at each radial position. Plots of maximum intensity (arbitrary units) as a function of diffraction angle are shown in FIGS. 13A and 13B.

Figure 13B:
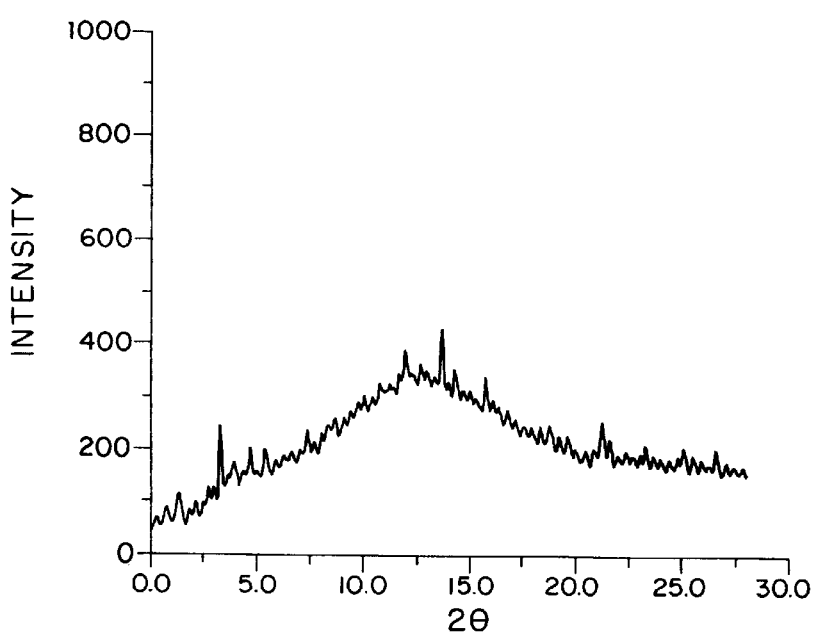

The characteristic peaks exhibited by crystalline ice are clearly visible in the crystalline sample (FIG. 13A), but these peaks do not appear in the laser treated sample (FIG. 13B). The laser melted and rapidly solidified ice does not show evidence of any crystalline peaks at the locations corresponding to the peaks of crystalline ice. The small peaks at various other angular locations may indicate small amounts of condensation on the surface of the slide, but the complete lack of spikes corresponding to the spikes in the crystalline ice sample proves that the sample is completely amorphous.

Additional samples studied show that the method produces amorphous ice in less dilute aqueous solutions, and even in pure water.

EXAMPLE 4

Vitrification of Human Erythrocytes

Applying a process similar to those used in Examples 2 and 3, a solution containing human erythrocytes was first frozen, then warmed with radiant energy and rapidly refrozen to vitrify the erythrocytes. Unprotected human erythrocytes were diluted in a phosphate buffered saline and bovine calf serum solution and frozen at a cooling rate of about 10,000° C./minute, resulting in a large amount of intracellular ice formation. A group of frozen cells were treated with conventional thawing procedures with warming rates of up to 80,000° C./minute—all of these cells lysed.

Another group of frozen cells were treated with a pulse from a Q-switched YAG laser at 532 nm so that the intracellular solution (which absorbs 532 nm radiation) melted; but the extracellular solution (which is transparent to 532 nm radiation) did not melt. The vitrification studies described in Examples 2 and 3 above show that this laser treatment leads to vitrification. The laser treated cells were then thawed using conventional protocols and 80% of the cells remained intact.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A method for vitrifying biological material comprising:
   (a) placing a biological material having a glass phase transition temperature in thermal contact with a cryogenically coolable environment;
   (b) cooling the cryogenically coolable environment to a temperature below the glass phase transition temperature of the biological material;
   (c) simultaneously with the cooling of the environment in thermal contact with the biological material, applying spatially confined heating using radiant energy to the biological material to maintain the temperature of at least a portion of the biological material at a physiological temperature of between about 0 to 40°;
   (d) stopping the application of spatially confined heating to the biological material to rapidly cool the and thereby vitrify the biological material.

2. The method of claim 1, wherein the cryogenically coolable environment is cooled to a temperature less than or equal to about 130 Kelvin degrees.

3. The method of claim 1, wherein stopping the application of spatially confined heating results in a cooling rate equal to or greater than about $10^{5°}$ C./second for the biological material.

4. The method of claim 1, wherein stopping the application of spatially confined heating results in a cooling rate equal to or greater than about $10^{6°}$ C./second for the biological material.

5. The method of claim 1, further comprising the step of recovering the vitrified biological material by warming the material at a sufficiently high rate to prevent the occurrence of devitrification.

6. The method of claim 1, wherein the radiant energy is at least partially absorbed by water within the biological material.

7. The method of claim 6, wherein the biological material is suspended in a medium that does not absorb the radiant energy.

8. The method of claim 1, wherein the radiant energy is at least partially absorbed by the biological material.

9. The method of claim 8, wherein the biological material is suspended in an aqueous solution.

10. The method of claim 1, wherein the radiant energy is in the form of a focused beam aimed toward at least a portion of the biological material.

11. The method of claim 10, wherein the radiant energy is supplied using a laser.

12. The method of claim 10, wherein the biological material is suspended in thermal contact with a cryostage.

13. The method of claim 12, wherein there is an adiabatic region between at least a portion of the biological material suspension and the cryostage.

14. A method for vitrifying cellular material comprising:
    (a) suspending a cellular material having a glass phase transition temperature in a solution to form a cellular material solution;
    (b) cooling the cellular material solution to a temperature below the glass phase transition temperature of the cellular material while maintaining at least a portion of the cellular material at a temperature between about 0C and 40° C.; and
    (c) rapidly cooling the portion of the cellular material maintained at between about 0° C. and 40° C. to a temperature at or below the glass phase transition temperature of the cellular material at a cooling rate greater than about $10^{5°}$ C./second so as to vitrify the cellular material.

15. The method of claim 14, wherein the cooling rate is greater than about $10^{6°}$ C./second.

16. The method of claim 14, wherein the cellular material solution is cooled by placing the cellular material solution in thermal contact with a cryogenically coolable environment that is maintained at a temperature below the glass phase transition temperature of the cellular material.

17. The method of claim 16, wherein the cellular material is maintained at a temperature between about 0° C. and 40° C. by applying spatially confined heating to the cellular material solution.

18. The method of claim 17, wherein the cellular material is rapidly cooled by suddenly stopping the spatially confined heating.

19. The method of claim 17, wherein the spatially confined heating consists of radiant energy directed to the cellular material solution.

20. The method of claim 19, wherein the radiant energy is in the form of a beam focused on at least a portion of the cellular material solution.

21. The method of claim 19, wherein the radiant energy is of a wavelength that is at least partially absorbed by the cellular material.

22. The method of claim 19, wherein the radiant energy is of a wavelength that is at least partially absorbed by intracellular water within the cellular material.

23. The method of claim 14, wherein at least a portion of the cellular material is cooled to below about 130 Kelvin degrees.

24. The method of claim 14, wherein the cellular material solution is in thermal contact with a cryostage.

25. The method of claim 24, wherein there is an adiabatic region between at least a portion of the cellular material solution and the cryostage.

26. The method of claim 14, wherein the cellular material solution is in thermal contact with a cryogenically coolable environment by being suspended within a hole formed in a high thermal conductivity material.

* * * * *